United States Patent [19]
Born et al.

[11] Patent Number: 5,349,625
[45] Date of Patent: Sep. 20, 1994

[54] X-RAY DIAGNOSTICS INSTALLATION FOR PERIPHERAL ANGIOGRAPHY EXAMINATIONS

[75] Inventors: Hans-Joachim Born, Moehrendorf; Gerd Huettenrauch, Uttenreuth; Heinz-Joachim Link, Erlangen, all of Fed. Rep. of Germany

[73] Assignee: Siemens Aktiengesellschaft, Munich, Fed. Rep. of Germany

[21] Appl. No.: 29,543

[22] Filed: Mar. 11, 1993

[30] Foreign Application Priority Data

Mar. 27, 1992 [DE] Fed. Rep. of Germany ....... 4210120

[51] Int. Cl.5 .............................................. G21K 5/10
[52] U.S. Cl. ...................................... 378/95; 378/146; 378/195
[58] Field of Search ................... 378/165, 99, 109, 110, 378/111, 112, 115, 116, 146, 151, 159, 97, 98, 91, 95, 150, 195, 197, 193, 152, 208, 20, 177, 8

[56] References Cited

U.S. PATENT DOCUMENTS

| | | |
|---|---|---|
| 5,050,199 | 9/1991 | Watanabe .............................. 378/146 |
| 5,231,651 | 7/1993 | Ozaki et al. ............................. 378/99 |

*Primary Examiner*—David P. Porta
*Assistant Examiner*—Don Wong
*Attorney, Agent, or Firm*—Hill, Steadman & Simpson

[57] ABSTRACT

An x-ray diagnostics installation for peripheral angiography examinations includes a control unit having an arithmetic unit that, on the basis of subject-related data supplied thereto, effects a pre-setting of the electrical parameters of the installation required for every exposure, plus the step length and the number of steps of the relative adjustment of the exposure unit and the patient support relative to one another, as well as the required diaphragm setting. By virtue of the pre-setting, stress on the patient is reduced, and since the overall time per examination is also reduced, patient throughput can be increased.

12 Claims, 5 Drawing Sheets

X-RAY DIAGNOSTICS INSTALLATION FOR PERIPHERAL ANGIOGRAPHY EXAMINATIONS

BACKGROUND OF THE INVENTION

1. Field of the Invention

The present invention is directed to an x-ray diagnostics installation of a type suitable for conducting peripheral angiography examinations.

2. Description of the Prior Art

X-ray diagnostics installations for conducting peripheral angiography examinations, i.e., of blood vessels in the extremities of a patient, generally include a pick-up unit composed of a radiation transmitter and radiation receiver, and a support means for an examination subject, with the pick-up unit and the support means being spatially adjustable as well as adjustable relative to one another via suitable means. The radiation transmitter can be supplied with energy via a control means, causing the emission of a ray beam. If the radiation receiver is executed as an image intensifier, it is followed by a video chain, so that an image of an examination region can be produced. A gating device is provided in the beam path of the ray beam with which the emitted ray beam can be gated onto the examination region. An automatic exposure unit controls the energy supply of the radiation transmitter such that a radiation shadowgram produced during transirradiation of the examination subject can be converted into a visible, easily interpreted image. If the radiation receiver is an x-ray film changer, it can be provided with an automatic exposure unit to insure that every exposure has the correct degree of blackening.

A peripheral angiography examination requires complicated and time-consuming programming measures for producing the exposure sequence, for the exact setting of the support means and diaphragm system as well as for defining the required range of displacement of the pick-up unit or of the support means.

To this end, in conventional systems the patient, support means, pick-up unit, diaphragm system and automatic exposure unit are configured and optimized for the successive exposures with respect to the image quality, the patient position and the examination region. This typically results in physical stress on the patient is thus considerable; moreover, the number of possible examinations that can be carried out daily is reduced.

German Patent 39 19 473 discloses an x-ray diagnostics installation for angiography, wherein a standard pre-setting of the x-ray dose, gating of the x-radiation, as well as the number and direction of the relative dislocations of the patient support and pick-up means ensue on the basis of a program for every exposure of a body section to be examined.

SUMMARY OF THE INVENTION

It is an object of the present invention to provide an x-ray diagnostics installation for conducting peripheral angiography examinations wherein the physical stress on the patient is reduced when producing the exposure sequence and with which the number of examinations possible on a daily basis is increased.

This object is achieved in accordance with the principles of the present invention in a peripheral angiography system having a control unit which includes an arithmetic unit that undertakes a calculation for pre-setting one or more system components matched to the examination subject, based on subject-related data (size, weight, shape, etc.).

The advantage of the invention is that an optimized examination program can thus be produced for the patient, so that the time consumed for producing the exposure sequence is greatly reduced. The physical stress on the patient is likewise reduced due to the low time expenditure. Mis-adjustments of the pick-up unit and support device are thus avoided, so that the radiation stress on the patient as well as stressing of the patient by injections of contrast agent are reduced.

Preferably, for further time-saving and reduction of the stress on the patient, the arithmetic unit calculates the diaphragm setting required for every exposure, and/or calculates the parameters of the radiation transmitter required for every exposure, and/or takes the format of the radiation receiver as well as the focus-to subject and focus-to radiation receiver spacing into consideration in making the calculation. The arithmetic unit may be followed by a display means for displaying the contour of the examination subject, the image size in the subject plane, the diaphragm settings and the radiation field with reference to the examination subject for every exposure position.

DESCRIPTION OF THE PREFERRED EMBODIMENTS

Figure 1:
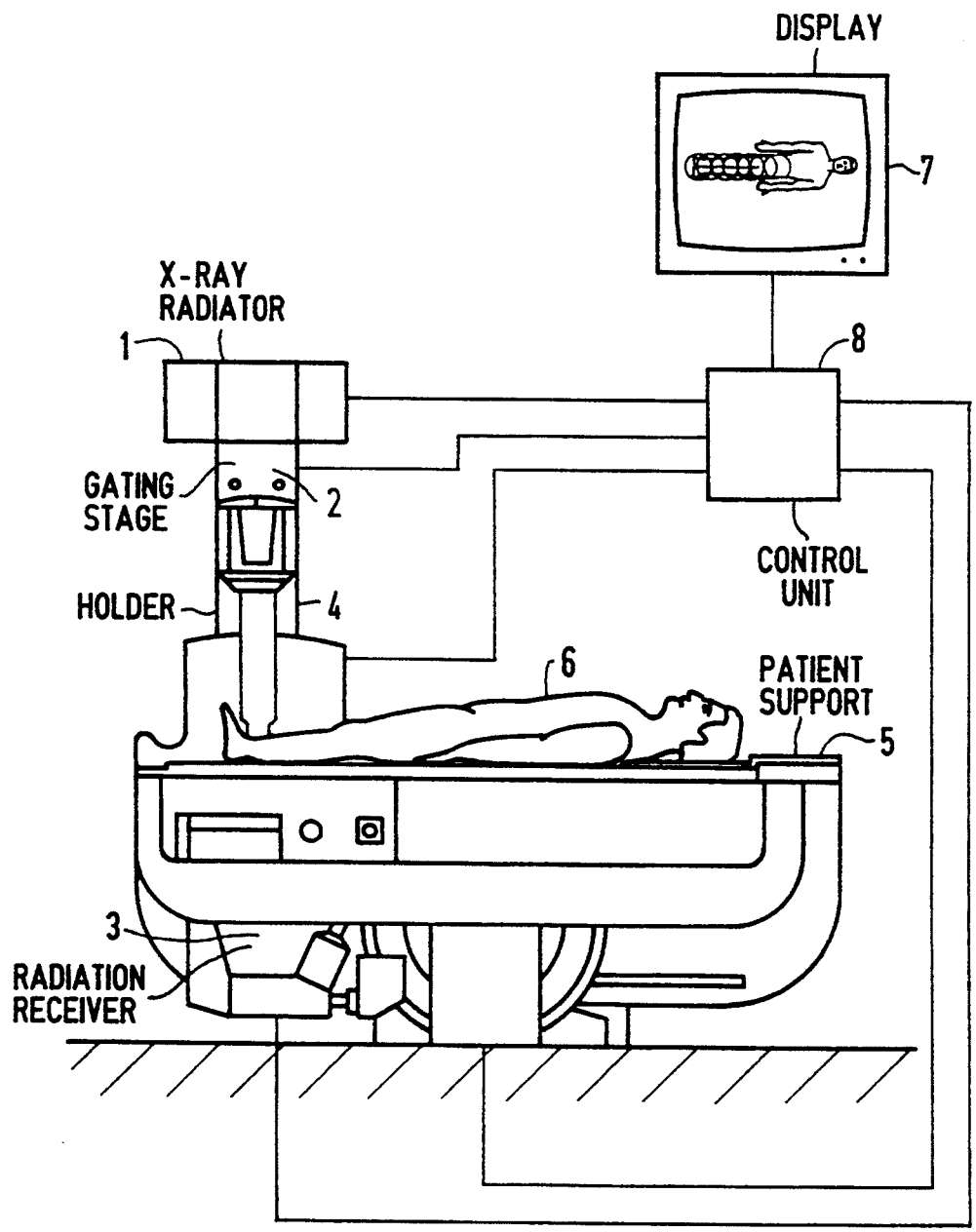
FIG. 1 is an x-ray diagnostics installation for peripheral angiography constructed in accordance with the principles of the present invention, shown schematically.

The x-ray diagnostics installation shown in FIG. 1 includes a pick-up unit composed of an x-ray radiator 1 having a gating stage 2, and a radiation receiver 3, which are held opposite one another by a holder 4. The holder 4 is constructed such that the pick-up unit is adjustable along a support 5 for an examination subject 6. Of course, such an x-ray diagnostics installation can also be executed such that the pick-up unit is stationary and the support 5 is adjustable. It is only necessary that the pick-up unit and the support 5 are adjustable relative to one another, so that a sequence of exposures of an examination region can be produced. The drive of the x-ray radiator I for 1 emission of a ray beam, the gating stage 2 for gating the ray beam, the adjustment of the pick-up unit or of the support 5 relative to one another, as well as the production of an image from the examination region of the examination subject 6 from the signals of the radiation receiver 3 on a display 7, ensue under the control of a control unit 8, the details of which shall be set forth in greater detail below with reference to FIG. 2.

Figure 2:
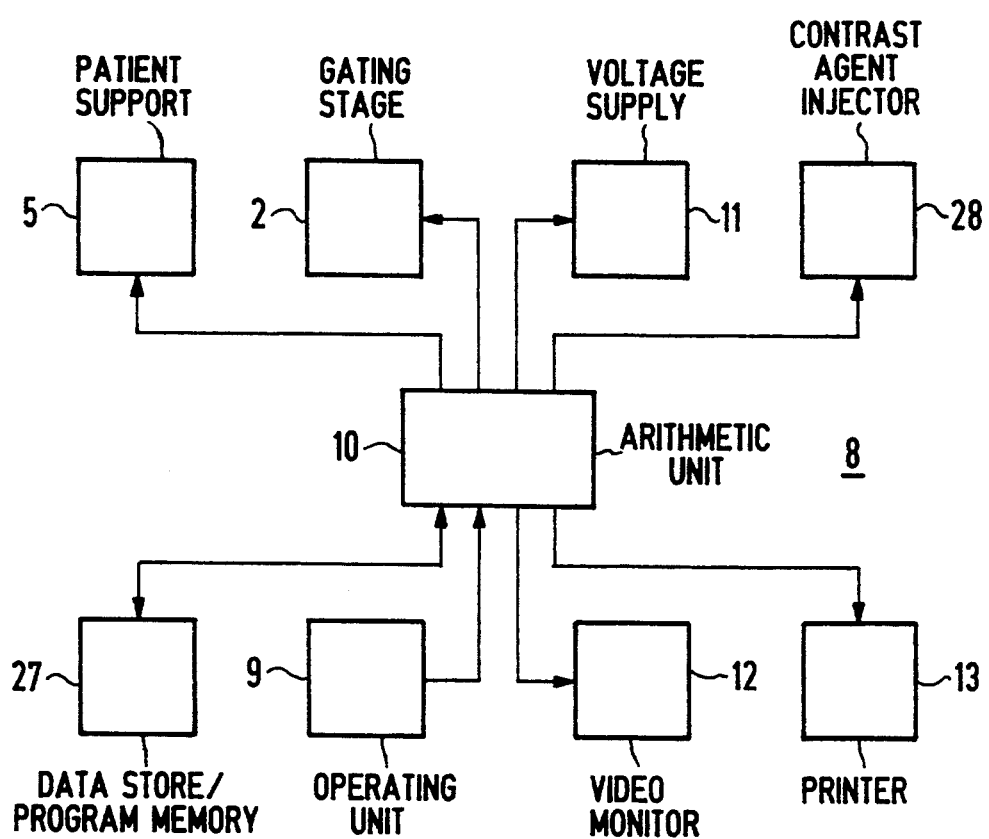
FIG. 2 is a schematic block diagram of a control unit of the invention for the x-ray diagnostics installation of FIG. 1.

As shown in FIG. 2, the control unit 8 includes an operating unit 9 by means of which subject-related data, for example the size, the weight and the physique (thin, average, fat; short, average, tail) of an examination subject 6 can be supplied to an arithmetic unit 10. When, for example, the leg of the patient is to be examined, the arithmetic unit 10 calculates the average length of the leg on the basis of this data, and also calculates the number of exposures to be produced resulting therefrom, the step length of the relative adjustment of pick-up unit and support 5 relative to one another, the electrical parameters required for every exposure, and the diaphragm setting of the gating stage 2 arranged in the beam path of the x-ray beam that is required for every exposure. A pre-setting of the means for the relative adjustment of pick-up unit or support 5, the gating stage 2, and a voltage supply 11 which feeds the x-ray radiator 1, ensues by the arithmetic unit 10 on the basis of the calculated data for each of the successive exposures.

Further apparatus-related parameters, for example the radiation receiver format as well as the apparatus geometry (focus-to-subject spacing and focus-to-image receiver spacing) and the desired section width and overlap, can be introduced into this calculation. These apparatus-related parameters can be input entered via the operating unit 9, insofar as they cannot be called as data of a memory of the control unit 8.

If the x-ray diagnostics installation includes a digital image processing system, the subject-related data and the apparatus-related parameters can be supplied from the image processing system to the arithmetic unit 10 within the framework of the invention.

Figure 3:
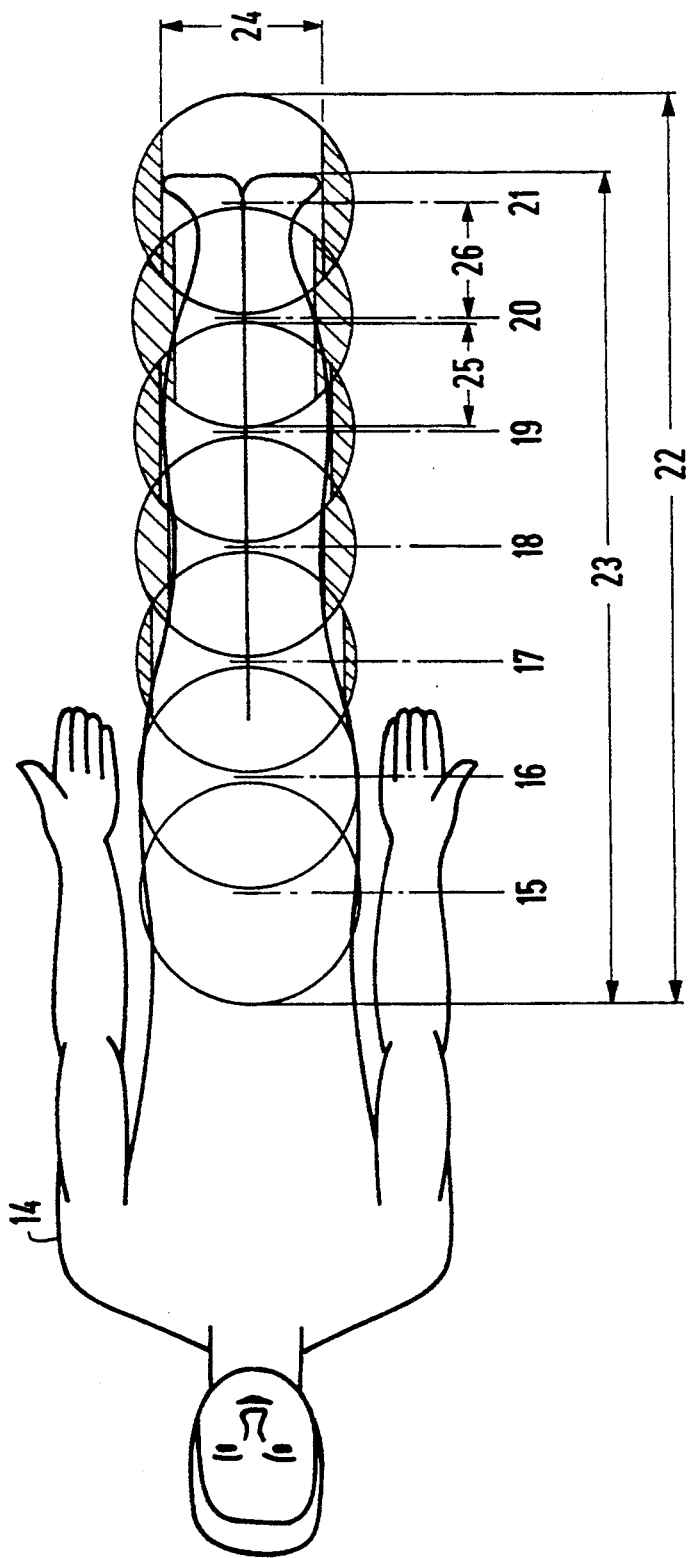
FIG. 3 shows a subject contour on a display means of the control unit of FIG. 2, as an example.

The display 7 can be in the form of a monitor 12, a printer 13 or a display field of the operating unit 9, so that, as shown in FIG. 3, the subject contour 14, the individual exposure positions 15 through 21, the diaphragm settings in the exposure positions 15 through 21 (shown shaded) the image size in the subject plane, as well as the pick-up regions of the subject relative to the radiation field of the radiation beam calculated from the subject-related data and from the apparatus-related parameters are displayed. In addition, the entire presentation region 22 in the subject plane, the usable presentation region 23 in the subject plane, the section width 24 in the subject plane, the overlap 25 in the subject plane, the step length 26, the number of steps and the image format or formats related to the subject plane can also be indicated or displayed.

The starting point for the calculation is a patient-related, anatomically typical, reproducible basic setting of the exposure unit, for example to the navel, that can be easily set under optical sighting supervision as the origin for the coordinates of the patient relative to the pick-up system.

Of course, these presentations and data can also be displayed on an x-ray monitor on which an image of the examination region can also be portrayed. The data calculated by the arithmetic unit 10 can be supplied in subject-related fashion to a data memory 27, so that these can in turn be called in as needed. It is thus possible to produce repeatable, subsequent examinations under identical system conditions for a patient.

Within the framework of the invention, the parameters of a contrast agent injector 28 required for the examination can likewise be calculated by the arithmetic unit 10 and can be pre-set via the control unit 8.

Figure 4:
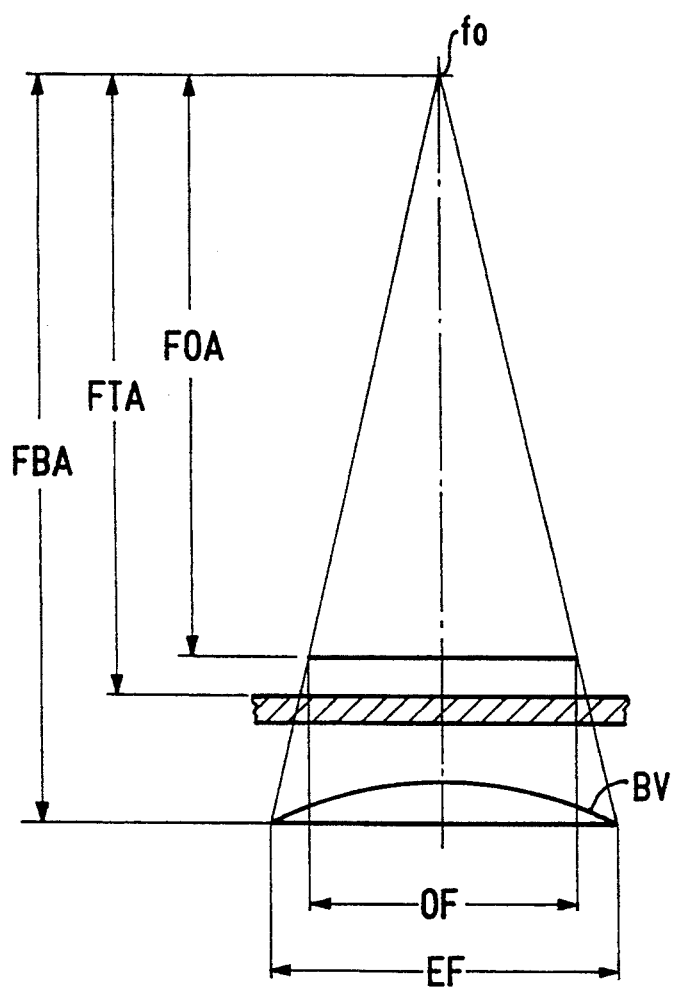
FIGS. 4 and 5 illustrate various parameters and other factors used by the arithmetic unit within the control unit in accordance with the principles of the present invention.
Figure 5:
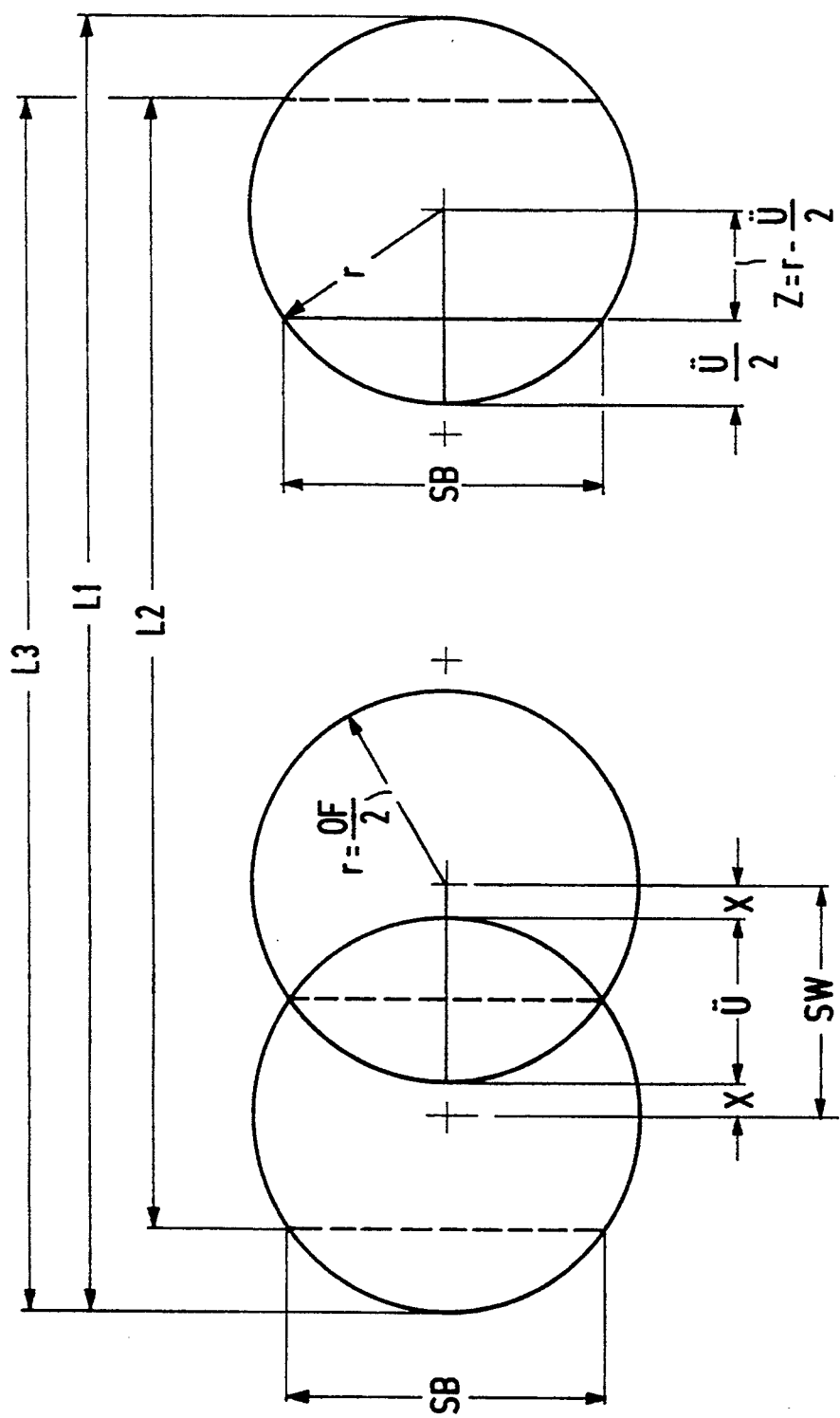

The arithmetic operations implemented in the arithmetic unit 10 for the pre-setting of the x-ray diagnostics installation for the exposure sequence are set forth below, with reference to FIGS. 4 and 5.

$OF = (EF/FBA)FOA$, or $OF = EF/V$;
$X = SW - r$, with $r = OF/2$;
since also $X = r - U$, then $U = SW - ZX$;
$Z = OF/2 - U/2 = r - U/2$;
$SB = 2[(OF/2)^2 - (OF/2 - U/2)^2]^{\frac{1}{2}} = 2(r^2 - Z^2)^{\frac{1}{2}}$;
$L_1 = SZ \cdot SW + OF$;
$L_2 = SZ \cdot SW + OF - U + SZ \cdot SW + 2Z$; and
$L_3 = L_2 + U/2$;
wherein;
FOA = focus-to-subject distance
FTA = focus-to-table distance
FBA = focus-to-image intensifier distance in the plane of the blanking
OF = subject field
EF = input field of the image intensifier
U = overlap
SW = step width
SZ = number of steps
SB = section width
$L_1$ = overall subject length
$L_2$ = subject length between the section widths
$L_3$ = medically usable region
V = magnification factor
Z = pick-up field in the subject plane
X and r are parameters shown in FIG. 5.

According to a first exemplary embodiment of the invention, an image intensifier input field of 40 cm, a focus-to-image intensifier distance of 123 cm, a focus-to-subject distance of 100 cm, a step length of 20 cm, and a number of steps of 5, are to be entered into the arithmetic unit 10 via the operating unit 9, as a numerical example.

On the basis of these inputs, the arithmetic unit 10 then implements the arithmetic operations 1 through 6 recited below:

| | | |
|---|---|---|
| 1. OF | = (EF/FBA)FOA | |
| | = (40 cm/123 cm)100 cm | |
| | = 32.52 cm | |
| 2. r | = OF/2 | |
| | = 32.52 cm/2 | |
| | = 16.26 cm | |
| 3. X | = SW − r | |
| | = 20 cm − 16.26 cm | |
| | = 3.74 cm | |
| 4. U | = SW − 2X | |
| | = 20 cm − 2(3.74 cm) | |
| | = 12.52 cm | |
| 5. SB | = 2[(OF/2)² − (OF/2 − U/2)²]^½ | |
| | = 2[(16.26 cm)² − (16.26 − 12.52/2)²]^½ | |
| | = 25.64 cm | |
| 6. L₃ | = SZ · SW + OF − U + U/2 | |
| | = 5 · 20 cm + 32.52 cm − 12.52 cm + 6.26 cm | |
| | = 126.26 cm | |

The table recited below can be displayed on the display 7:

| | |
|---|---|
| overlap = | 12.52 cm |
| section width = | 25.64 cm |
| usable examination region = | 126.26 cm. |

According to another exemplary embodiment of the invention, three keys (short, average, tall) are provided at the operating unit 9, which are to be operated in conformity with the physique of the patient to be examined.

Upon actuation of a key, the arithmetic unit 10 interrogates a corresponding memory of a data store and, given examination of the leg of a patient as an example, thus obtains the following data for further calculation:

| | |
|---|---|
| key "short" = | 105 cm, |
| key "average" = | 115 cm, |
| key "tall" = | 130 cm. |

Of course, it is also possible within the framework of the invention to enter the actual length/width of the overall examination region of the subject (leg) via the operating unit 9.

Further data corresponding to the apparatus geometry can be stored in the data store as permanent values, these being interrogated by the arithmetic unit 10 and being capable of being utilized for the calculation. Permanent values for the apparatus geometry are the image intensifier input field, the focus-to-image intensifier spacing, the focus-to-subject spacing, the overlap and the section width.

The arithmetic unit 10 thus calculates the optimum number of steps.

According to a third exemplary embodiment of the invention, it is possible in an expansion of the second exemplary embodiment to prescribe the desired overlap and/or the section width via the operating unit 9, which then enters into the calculation.

It is possible within the framework of the invention to define the subject contour via suitable separate means and to supply the subject-related data thus obtained to the arithmetic unit 10 on a disk or in some other stored form for further calculation.

The pre-setting of the gating stage 2 likewise ensues on the basis of subject-related data, for example by the arithmetic unit 10—on the basis of subject-related data "short, average, tall; thin, average, fat)—interrogating corresponding data of a data store, so that the gating stage 2 is then correspondingly driven via the control unit 8. Data corresponding to the following table for gatings with reference to the example of exposure positions 15 through 21 can be contained in the data store:

| | Exposure Position | | | | | | |
|---|---|---|---|---|---|---|---|
| | 15 | 16 | 17 | 18 | 19 | 20 | 21 |
| thin | 40 cm | 40 cm | 38 cm | 33 cm | 35 cm | 30 cm | 31 cm |
| average | 40 cm | 40 cm | 40 cm | 35 cm | 37 cm | 32 cm | 33 cm |
| fat | 40 cm | 40 cm | 40 cm | 38 cm | 39 cm | 36 cm | 37 cm |

The pre-setting of the voltage supply 11 likewise ensues on the basis of the entry of subject-related data. The arithmetic unit 10 for this purpose also interrogates a data store that contains data of electrical parameters corresponding to the subject-related data, so that the control unit 8 then correspondingly drives the voltage supply 11.

A display or an output in some other form of the calculated data on a monitor or printer in tables and/or graphic presentation is possible in accord with all exemplary embodiments of the invention.

Although modifications and changes may be suggested by those skilled in the art, it is the intention of the inventors to embody within the patent warranted hereon all changes and modifications as reasonably and properly come within the scope of their contribution to the art.

We claim as our invention:

1. An x-ray diagnostics installation for peripheral angiography comprising:

an x-ray exposure means for generating an x-ray beam and for detecting said x-ray beam after passage through a patient to obtain an x-ray exposure of said subject, said x-ray exposure unit including diaphragm means for selectively gating said x-ray beam;

a support unit for receiving a patient to be examined using said x-ray exposure means, said support unit and said x-ray exposure means being relatively movable through a plurality of steps each having a step length with an exposure of said patient being obtained by said x-ray exposure means at each of said steps to obtain a plurality of successive exposures; and control means connected to said x-ray exposure means and to said support unit for controlling operation of said x-ray exposure means and said support unit, including controlling said diaphragm means, said control means including arithmetic means for calculating values for pre-setting one or more of said plurality of successive exposures, said step length and said plurality of steps matched to said patient based on subject-related data including the size, weight and physique of said patient.

2. An x-ray diagnostics installation as claimed in claim 1 wherein said x-ray exposure means includes an x-ray radiator having a focus, and a radiation receiver, and wherein said arithmetic means comprises means for employing a focus-to-patient distance and a focus-to-radiation receiver distance in calculating said values for pre-setting by said control means in combination with said subject-related data.

3. An x-ray diagnostics installation as claimed in claim 1 wherein said control means includes display means for displaying a contour of said patient in a patient plane, a setting of said diaphragm means and a setting of the radiation field of said x-ray exposure unit with reference to said patient for each exposure position in said plurality of successive exposures.

4. An x-ray diagnostics installation as claimed in claim 3 wherein said display means is a video monitor.

5. An x-ray diagnostics installation as claimed in claim 3 wherein said display means is a printer.

6. An x-ray diagnostics installation as claimed in claim 3 wherein said control means includes an operating unit and wherein said display means is a display field of said operating unit.

7. An x-ray diagnostics installation as claimed in claim 1 wherein said installation has system-related distance parameters, and wherein said control means includes a memory, connected to said arithmetic means, in which said distance parameters, said step length, said plurality of steps, and standard settings for said diaphragm means are stored for use by said arithmetic means.

8. An x-ray diagnostics installation as claimed in claim 1 further comprising video chain means for generating and processing a digital image of said patient, for obtaining and supplying said patient-related data to said arithmetic means.

9. An x-ray diagnostics installation as claimed in claim 1 wherein said exposures in said plurality of exposures have an overlap and said installation further comprising means for supplying data corresponding to a selected overlap to said arithmetic means for use in calculating said values for pre-setting by said control means.

10. An x-ray diagnostics installation as claimed in claim 1 wherein said exposures in said plurality of exposures have a section with said installation further comprising means for supplying data corresponding to a selected section with said arithmetic means for use in calculating said values for pre-setting by said control means.

11. An x-ray diagnostics installation as claimed in claim 1 further comprising memory means for storing data for a specified patient and pre-settings associated with said specified patient for re-use in subsequent examinations of said specified patient.

12. An x-ray diagnostics installation as claimed in claim 1 wherein said x-ray exposure means and said patient support define an examination region, and further comprising means for supplying data corresponding to a selected examination region to said arithmetic means for use in calculating said values for pre-setting by said control means.

* * * * *